(12) United States Patent
Kennedy et al.

(10) Patent No.: US 7,964,693 B2
(45) Date of Patent: Jun. 21, 2011

(54) PHOTOCURABLE POLYMERS FOR OPHTHALMIC APPLICATIONS

(75) Inventors: Joseph P. Kennedy, Akron, OH (US); Yaohong Chen, Fairlawn, OH (US)

(73) Assignee: The University of Akron, Akron, OH (US)

( * ) Notice: Subject to any disclaimer, the term of this patent is extended or adjusted under 35 U.S.C. 154(b) by 376 days.

(21) Appl. No.: 12/094,005

(22) PCT Filed: Dec. 29, 2006

(86) PCT No.: PCT/US2006/049611
§ 371 (c)(1), (2), (4) Date: Aug. 7, 2008

(87) PCT Pub. No.: WO2007/079240
PCT Pub. Date: Jul. 12, 2007

(65) Prior Publication Data
US 2009/0203869 A1    Aug. 13, 2009

Related U.S. Application Data

(60) Provisional application No. 60/754,799, filed on Dec. 29, 2005.

(51) Int. Cl.
*C08G 77/12* (2006.01)
(52) U.S. Cl. .......................................... 528/31; 528/25
(58) Field of Classification Search .................... 528/31, 528/25
See application file for complete search history.

(56) References Cited

U.S. PATENT DOCUMENTS

| 6,124,418 A | 9/2000 | Crivello et al. |
| 6,824,266 B2 | 11/2004 | Jethmalani et al. |
| 7,534,901 B2 * | 5/2009 | Crivello ........................ 549/215 |
| 2004/0249181 A1 | 12/2004 | Cetin et al. |

OTHER PUBLICATIONS

Myoungsouk, Jang, et al, "Synthesis and Cationic Photopolymerization of Epoxy-Functional Siloxane Monomers and Oligomers", New york State Center for Polymer Synthesis, Dept. of Chemistry, Rensselaer Polytechnic Institute, Troy, New York 12180, vol. 41, 3056-3073 (2003) Wiley Periodicals, Inc.

* cited by examiner

*Primary Examiner* — Kuo-Liang Peng
(74) *Attorney, Agent, or Firm* — Daniel J. Schlue; Roetzel & Andress (57) ABSTRACT

The present invention generally relates to pre-polymer and polymer compositions that can be photopolymerized. In one embodiment, the present invention relates to crosslinking agents that can be used in the photopolymerization of the pre-polymers and polymers disclosed herein. In another embodiment, the present invention relates to processes for producing pre-polymer, polymer and crosslinking compositions useful in photopolymerization reaction schemes. In one instance, the pre-polymers and polymers of the present invention can be crosslinked via a suitable crosslinking agent to produce networks (e.g., amphiphilic networks and/or co-networks).

4 Claims, 3 Drawing Sheets

PHOTOCURABLE POLYMERS FOR OPHTHALMIC APPLICATIONS

FIELD OF THE INVENTION

The present invention generally relates to pre-polymer and polymer compositions that can be photopolymerized. In one embodiment, the present invention relates to crosslinking agents that can be used in the photopolymerization of the pre-polymers and polymers disclosed herein. In another embodiment, the present invention relates to processes for producing pre-polymer, polymer and crosslinking compositions useful in photopolymerization reaction schemes. In one instance, the pre-polymers and polymers of the present invention can be crosslinked via a suitable crosslinking agent to produce networks (e.g., amphiphilic networks and/or co-networks).

BACKGROUND OF THE INVENTION

Polymer compositions useful in ophthalmic lenses (e.g., contact lenses and/or intraocular lenses) are known in the art. However, there is a need in the art for new polymer materials with improved chemical and physical properties. For example, polymer compositions having improved oxygen permeability, optical clarity, and/or durability are needed. Also of interest would be polymer compositions that are fabricated via more environmentally friendly processes (e.g., polymer products that can be obtained via reduced emission and/or emission-free reactions).

Thus, there is a need in the art for improved polymer compositions that can be used in, among other things, contact lenses and/or intraocular lenses.

SUMMARY OF THE INVENTION

The present invention generally relates to pre-polymer and polymer compositions that can be photopolymerized. In one embodiment, the present invention relates to crosslinking agents that can be used in the photopolymerization of the pre-polymers and polymers disclosed herein. In another embodiment, the present invention relates to processes for producing pre-polymer, polymer and crosslinking compositions useful in photopolymerization reaction schemes. In one instance, the pre-polymers and polymers of the present invention can be crosslinked via a suitable crosslinking agent to produce networks (e.g., amphiphilic networks and/or co-networks).

In one embodiment, the present invention relates to a crosslinker composition comprising a compound according to the following formula:

wherein $X_1$, $X_2$, and $X_3$ are independently selected from linear alkyl chains having from 1 carbon to about 6 carbon atoms, and wherein $Y_1$, $Y_2$, and $Y_3$ are independently selected from linear aliphatic epoxide moieties, linear olefin epoxide moieties, cyclic aliphatic epoxide moieties, cyclic olefin epoxide moieties, or aromatic epoxide moieties.

In another embodiment, the present invention relates to a composition comprising a compound according to the following formula:

$$C_1-(B_1-B_2-B_3)_t-C_2$$

wherein $C_1$ and $C_2$ are each independently selected from identical or different crosslinking moieties having at least one epoxide moiety therein, wherein $B_1$, $B_2$, and $B_3$ are each independently selected from identical or different polymer blocks, and wherein t is an integer from 1 to about 250.

In still another embodiment, the present invention relates to a composition comprising two or more different repeating tri-block structures terminated by $C_1$ and $C_2$, wherein $C_1$ and $C_2$ are each independently selected from identical or different crosslinking moieties having at least one epoxide moiety therein, and the repeating tri-block structures are selected from (PEG-PEG-PEG)$_t$, (PDMS-PEG-PEG)$_t$, (PEG-PDMS-PEG)$_t$, (PEG-PEG-PDMS)$_t$, (PDMS-PDMS-PEG)$_t$, (PDMS-PEG-PDMS)$_t$, (PEG-PDMS-PDMS)$_t$, (PDMS-PDMS-PDMS)$_t$, where each t is independently an integer from 1 to about 250. In another embodiment, such a compound has three, four, five, six, seven, or even eight different repeating tri-block structures. Non-limiting example of compounds that fall within the scope of this embodiment include, but are not limited to, $C_1$-(PEG-PEG-PEG)$_t$-(PDMS-PEG-PEG)$_t$-$C_2$, and

$C_1$-(PDMS-PEG-PEG)$_t$-(PEG-PDMS-PEG)$_t$(PEG-PEG-PDMS)$_t$-$C_2$.

In still another embodiment, the present invention relates to a network composition comprising a compound according to the following formula:

wherein $X_1$, $X_2$, $X_3$, $X_4$, $X_5$, and $X_6$ are independently selected from linear alkyl chains having from 1 to about 6 carbon atoms, wherein $Y_1$, $Y_2$, $Y_3$, $Y_4$, $Y_5$, and $Y_6$ are independently selected from crosslinked linear aliphatic epoxide moieties, crosslinked linear olefin epoxide moieties, crosslinked cyclic aliphatic epoxide moieties, crosslinked cyclic olefin epoxide moieties, or crosslinked aromatic epoxide moieties, wherein $B_1$, $B_2$ and $B_3$ are each independently selected from identical or different polymer blocks, and wherein t is an integer from 1 to about 250.

In yet another embodiment, the present invention relates to a network composition comprising a compound according to the following formula:

wherein $X_1$, $X_2$, $X_3$, $X_4$, $X_5$, and $X_6$ are independently selected from linear alkyl chains having from 1 to about 6 carbon atoms, wherein $Y_1$, $Y_2$, $Y_3$, $Y_4$, $Y_5$, and $Y_6$ are independently selected from crosslinked linear aliphatic epoxide moieties, crosslinked linear olefin epoxide moieties, crosslinked cyclic aliphatic epoxide moieties, crosslinked cyclic olefin epoxide moieties, or crosslinked aromatic epoxide moieties, and wherein the repeating tri-block structure represented by —[$B_1$—$B_2$—$B_3$]— comprises two or more different repeating tri-block structures selected from (PEG-PEG-PEG)$_t$, (PDMS-PEG-PEG)$_t$, (PEG-PDMS-PEG)$_t$, (PEG-PEG-PDMS)$_t$, (PDMS-PDMS-PEG)$_t$, (PDMS-PEG-PDMS)$_t$, (PEG-PDMS-PDMS)$_t$, (PDMS-PDMS-PDMS)$_t$, where each t is independently an integer from 1 to about 250. In another embodiment, such a compound has three, four, five, six, seven, or even eight different repeating tri-block structures.

In still yet another embodiment, the present invention relates to an intraocular lens and/or contact lens comprising a compound according to the following formula:

wherein each Z is independently selected from:

produce networks (e.g., amphiphilic networks and/or co-networks).

Photoinitiated cationic crosslinking polymerizations of multifunctional epoxides are of great interest and importance in many industrial applications. First, the ability to conduct these crosslinking polymerizations very rapidly with low energy and without the use of inert atmosphere, presents significant economic advantages. Second, no emission results from the solvent-free polymerization. Third, the resulting networks have improved thermal, mechanical and chemical resistance, high oxygen permeability, low shrinkage and excellent biocompatibility.

Polydimethylsiloxane (PDMS) possesses high oxygen permeability, optical transparency and excellent biocompatibility. However, the low modulus of elasticity limits its direct application for intraocular lens (IOL) in the absence of filler reinforcement. According to one embodiment of the present invention, the mechanical properties of a homo-PDMS network can be improved by using one or more of a class of crosslinkers defined by the following general structure.

(1)

DETAILED DESCRIPTION OF THE INVENTION

Figure 1:
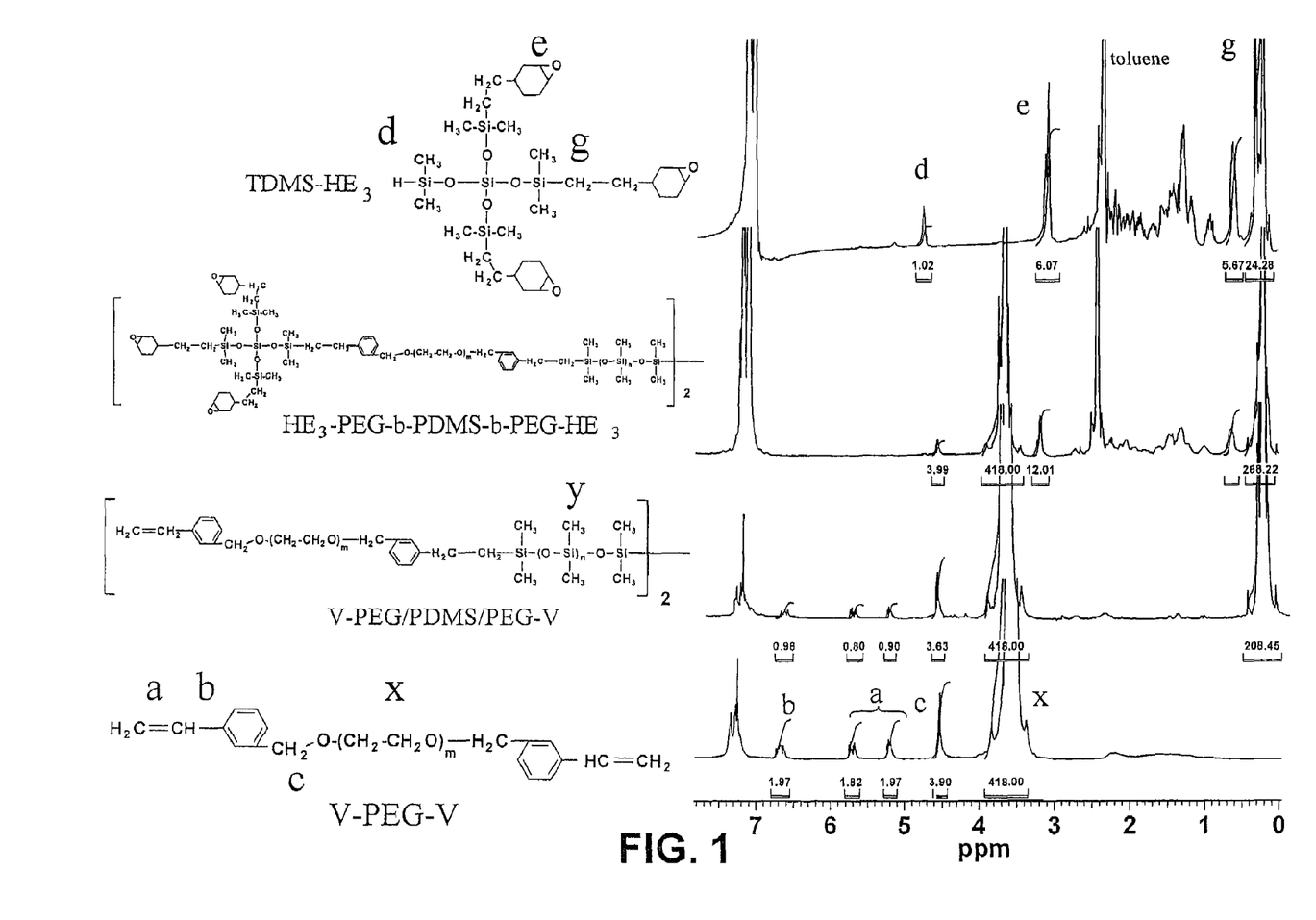
FIG. 1 is a set of NMR spectra of various embodiments and components of the present invention.
Figure 2:
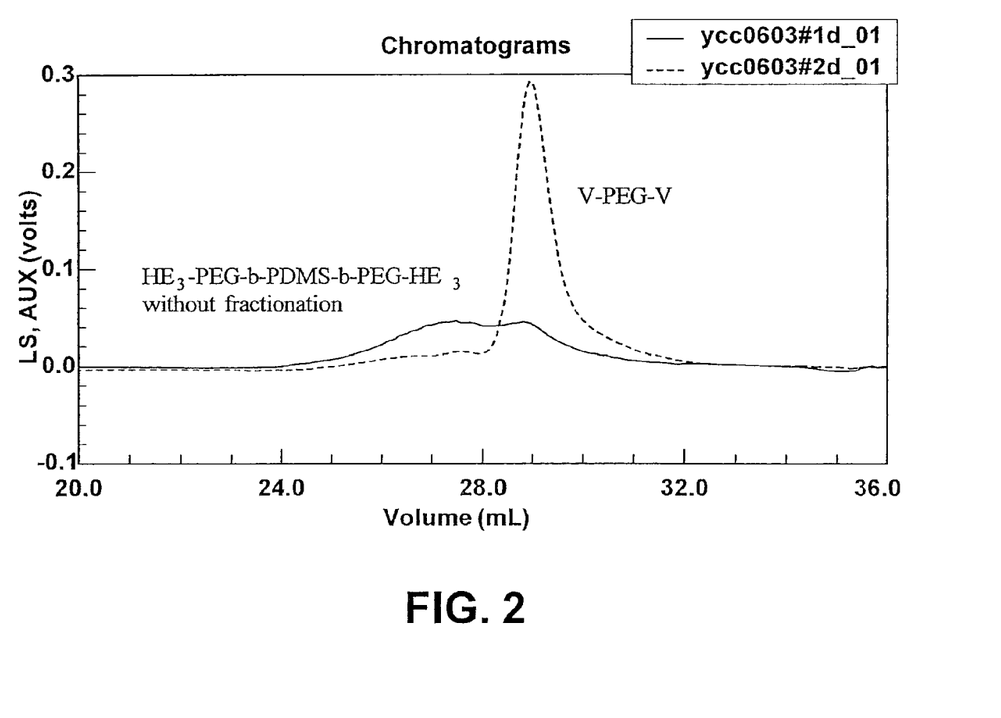
FIG. 2 is a set of chromatograms of a V-PEG-V component, and an $HE_3$-PEG-b-PDMS-b-PEG-$HE_3$ prepolymer.
Figure 3:
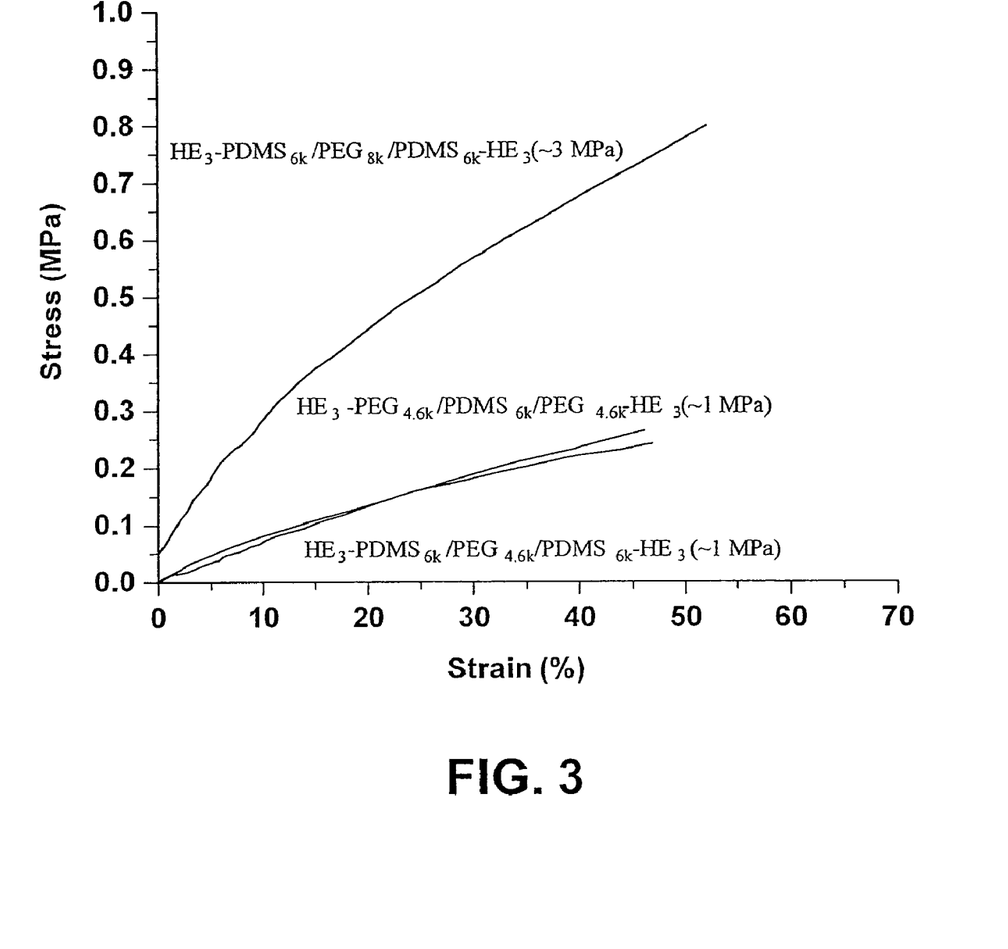
FIG. 3 is a set of stress strain curves for three different example embodiments.

The present invention generally relates to pre-polymer and polymer compositions that can be photopolymerized. In one embodiment, the present invention relates to crosslinking agents that can be used in the photopolymerization of the pre-polymers and polymers disclosed herein. In another embodiment, the present invention relates to processes for producing pre-polymer, polymer and crosslinking compositions useful in photopolymerization reaction schemes. In one instance, the pre-polymers and polymers of the present invention can be crosslinked via a suitable crosslinking agent to wherein, in one embodiment, $X_1$, $X_2$ and $X_3$ are independently selected from an alkyl or alkenyl moiety. In one embodiment, such alkyl or alkenyl moieties can be linear. In another embodiment, $X_1$, $X_2$ and $X_3$ are independently selected from alkyl moieties having from 1 to about 6 carbon atoms. In some embodiments $X_1$, $X_2$ and $X_3$ are all alkyl moieties having 2 carbon atoms. According to one embodiment, $Y_1$, $Y_2$, and $Y_3$ can each be independently selected from one or more epoxide moieties. In one embodiment, the epoxide moieties are selected from one or more of aliphatic epoxides, linear olefin epoxides, cyclic aliphatic epoxides, cyclic olefin epoxides, aromatic epoxides, substituted epoxides, or multifunctional epoxides. In another embodiment, $Y_1$, $Y_2$, and $Y_3$ can each comprise a cyclohexyl epoxide moieties.

In one embodiment, a suitable crosslinking composition for use in conjunction with the present invention can comprise tetrakis(dimethylsiloxyl) silane (TDMS-$HE_3$). This crosslinker comprises three epoxycyclohexyl groups and one silicon hydride (Si—H) group. A synthesis of TDMS-$HE_3$ is diagrammatically shown in Reaction Scheme 1.

Reaction Scheme 1

In one embodiment the product shown in Reaction Scheme 1 can be made according to the following example procedure. A 250 mL three-neck flask is provided, and fitted with a magnetic stirrer, a reflux condenser and addition funnel. The following reagents are added to the flask: 3.29 grams (0.01 mol) of tetrakis (dimethylsiloxy) silane (TDMSH), 10 mL of freshly distilled toluene, and approximately 5 to 7 milligrams of tri(triphenylphosphine) rhodium(I)chloride (Wilkinson's catalyst), The addition funnel is charged with 4-Vinyl-1-cyclohexene 1,2-epoxide (VHE) (3.72 grams, 0.03 mol) and the reagent is dripped into the reaction milieu. The temperature is raised to about 65° C. to 70° C. for about one day. The progress of the hydrosilation reaction can be followed by $^1$H-NMR (in ODd3) by monitoring of the disappearance of the VHE vinyl groups and/or the appearance of the product. The product, TDMS-HE$_3$, can either be recovered, or additional agents can be added to the reaction mixture and subsequent reactions carried as set forth in Reaction Scheme 2 below.

Reaction Scheme 2 outlines a synthesis strategy for preparing a novel intermediate HE$_3$-PDMS-HE$_3$ (i.e., compound 3), and a network structure made therefrom. Compound 3 can be made by hydrosilation of V-PDMS-V with TDMS-HE$_3$ in the presence of Wilkinson's (or Karstedt's) catalyst. As shown in Reaction Scheme 2, compound 3 can be photo-crosslinked to form a novel network structure according to the chemical formula for compound 4.

According to some embodiments, crosslinkers, such as structure 2 (i.e., the TDMS-HE$_3$ crosslinker), can be coupled with α,ω-vinyl terminated PDMS oligomer by hydrosilation, as shown in Reaction Scheme 2. This results in structure 3, which comprises a pair of three-armed star epoxides joined by PDMS through their silicon hydride moieties.

According to some embodiments, a homo-PDMS network, such as structure 4, can be formed by crosslinking a telechelic three-armed epoxided star structure, such as structure 3 (i.e., HE$_3$-PDMS-HE$_3$) as set forth in Reaction Scheme 2.

(4)

According to structure 4, each variable Z can vary independently and can comprise structure 4.1, 4.2, 4.3, 4.4, or 4.5.

4.1

4.2

4.3

4.4 and

4.5

In some embodiments, excess crosslinker (e.g., structure 2, TDMS-HE$_3$) can be photopolymerized as well. In some embodiments, photopolymerized excess crosslinker can reinforce a PDMS portion of the network, for example, as one or more nanoscale fillers. In one embodiment, the above-mentioned TDMS-HE$_3$ can function as both a crosslinker and filler.

The present invention is not limited to the above-mentioned silane crosslinking agent, which is merely one example embodiment. One of skill in the art would recognize that other suitable silane crosslinking compositions can also be used.

Reaction Scheme 2

(HE₃-PDMS-HE₃)
(3)

↓ hv (4)

In the context of Reaction Scheme 2, the variable "n" can be an integer from 1 to about 500. More particularly, "n" can be an integer from 1 to about 50, from about 50 to about 100, from about 100 to about 150, from about 150 to about 200, from about 200 to about 250, from about 250 to about 300, from about 300 to about 350, from about 350 to about 400, from about 400 to about 450, or even from about 450 to about 500. Here, as elsewhere in the specification and claims, individual range limits can be combined to produce additional ranges.

According to one embodiment the product of Reaction Scheme 2 can be prepared according to the following example procedure. Several additional reagents are added to the reaction mixture of Scheme 1. Namely, 30 grams (0.005 mol) V-PDMS-V ($M_n$=6000 g/mol) dissolved in 50 mL of freshly distilled toluene, and 0.44 milligrams Wilkinson's (or Karstedt's) catalyst. The temperature of the milieu is then raised to about 80° C. to 90° C. for about one day. The progress of the hydrosilation reaction can be followed by $^1$H-NMR, for example, by monitoring the disappearance of the V-PDMS-V vinyl end groups.

According to some embodiments, homo-poly(dimethylsiloxane) networks can be produced by photocuring processes. Furthermore, according to some embodiments, such networks are suitable for use in intraocular lenses and hydrophobic coatings.

Another embodiment relates to photocurable, two-phase amphiphilic network materials. Some variations of this embodiment can comprise polydimethylsiloxane. One of skill in the art will recognize that polydimethylsiloxane (PDMS) is characterized by a relatively high oxygen permeability, optical transparency and biocompatibility. Accordingly, some silicone-based hydrogel embodiments combine the high oxygen permeability of PDMS and the comfort, wetting and low deposit characteristics of non-silicone based hydrogels.

According to some embodiments, a two-phase amphiphilic network material can comprise at least one component that increases the hydrophilicity of the network material. Some embodiments can comprise methacrylate functionalized silicone that is copolymerized with hydrophilic monomers. One of skill in the art will recognize that copolymerizing methacrylate functionalized silicone with hydrophilic monomers typically results in turbid and/or opaque, phase separated materials. Some embodiments overcome this shortcoming of the prior art by combining at least one hydrophilic poly(ethylene glycol) (PEG) portion with at least one PDMS portion to create/yield an amphiphilic co-network (APCN) system.

Reaction Schemes 3 and 4 set forth a process for synthesizing such an APCN. Specifically, Reaction Scheme 3 sets forth an example synthesis of V-PDMS/PEG/PDMS-V tri-blocks bearing vinyl termini. According to some embodiments the tri-block can be subsequently coupled to two equivalents of TDMS-HE₃ and photocured to yield the product shown in Scheme 4. Note that the compounds 5, 7, and 9 have a reflection plane to the right of the drawn portion. However, rather than drawing the entire molecule, a subscript "2" is used as short hand.

Reaction Scheme 3

According to one embodiment, the process shown diagrammatically in Reaction Scheme 3 can be made according to the following example procedure V-PEG-V ($M_n$=4600 g/mol, 2.3 grams, 0.5 mmol) is dissolved in toluene (60 ml) in a 250 mL, three-neck flask fitted with a magnetic stirrer, a reflux condenser and addition funnel. The addition funnel is charged with DMSH (6.7 grams, 0.05 mol), which is dripped into the reaction milieu. A solution of Wilkinson's (or Karstedt's) catalyst (0.46 milligrams) is added to the reactor. The temperature is then raised to about 65° C. to 70° C. for about eight to twelve hours. The progress of the hydrosilation reaction can be followed by $^1$H-NMR (in $CDCl_3$), for example, by the monitoring of the disappearance of the V-PEG-V vinyl end groups. The resulting HSi-PEG-SiH compound can be isolated by removing the solvent in vacuo.

Another 250 mL three-neck flask is fitted with a magnetic stirrer, a reflux condenser and addition funnel. The vessel is charged with 2.3 grams (0.5 mmol) HSi-PEG-SiH, 6 grams (1 mmol) V-PDMS-V (6000 g/mol), and about 100 mL freshly distilled toluene, and 0.44 mg Wilkinson's (or Karstedt's) catalyst. The temperature is raised to about 80° C. to 90° C. for about 8 to 12 hours. The progress of the hydrosilation reaction can be followed by $^1$H-NMR (in $CDCl_3$), for example, by monitoring of the disappearance of the Si—H end groups of HSi-PEG-SiH. The resulting vinyl terminated structure (V-PDMS-b-PEG-b-PDMS-V) can be recovered by removing the solvent in vacuo.

Reaction Scheme 4 sets forth a synthesis of an end-functionalized triblock $HE_3$-PDMS-b-PEG-b-PDMS-$HE_3$ starting from the product of Reaction Scheme 3. Scheme 4 also shows photocrosslinking the product made thereby to form a novel network structure.

One suitable crosslinker that can be used in connection with some embodiments can comprise tetrakis(dimethylsiloxyl) silane. As noted above, tetrakis(dimethylsiloxyl) silane contains three epoxycyclohexyl groups and one Si—H group (TDMS-$HE_3$) and can be synthesized as shown in Reaction Scheme 1.

(9)

(TDMS-HE₃)

(2)

(HE₃-TDMS/PDMS/PEG/PDMS/TDMS-HE₃)

(10)

-continued (11)

Again, one of skill in the art will recognize that the present invention is not limited to solely the above-mentioned silane crosslinking agent. Other suitable silane crosslinking compositions can be used in conjunction with the present invention.

The V-PDMS-b-PEG-b-PDMS-V compound of Reaction Scheme 3 can be tethered to the crosslinker set forth in Reaction Scheme 1 according to the following procedure. Several reagents are added to the reaction mixture of Reaction Scheme 1. Namely, V-PDMS-b-PEG-b-PDMS-V dissolved in 100 mL freshly distilled toluene, and 0.44 milligrams Wilkinson's (or Karstedt's) catalyst. The temperature is raised to about 80° C. to 90° C. for about eight to twelve hours. The progress of the hydrosilation reaction can be followed by $^1$H-NMR (in CDCl$_3$), for example, by monitoring the disappearance of the vinyl end groups of V-PDMS-b-PEG-b-PDMS-V. The resulting structure (HE$_3$-PDMS-b-PEG-b-PDMS-HE$_3$) can be isolated by removing the solvent in vacuo.

A network structure can be made from HE$_3$-PDMS-b-PEG-b-PDMS-HE$_3$ by subjecting the structure to an amount and wavelength of electromagnetic radiation effective to result in crosslinking of the epoxide moieties. Similar to the foregoing examples, an excess of the TDMS-HE$_3$ crosslinker can be photopolymerized as well and thus reinforces the PDMS phase. The novel TDMS-HE$_3$, which functions as both crosslinker and filler, has a surprising effect on the mechanical properties of the PDMS/PEG network. Table 1 demonstrates the sol fraction and swelling degree of two hydrogels.

TABLE 1

Sol fraction and swelling degree of PDMS/PEG membranes

|  |  |  | Hydrogel 1 | Hydrogel 2 |
|---|---|---|---|---|
| HSi-PEG-SiH: | moles |  | 1:10:5 | 1:4:2 |
| TDMS-HE$_3$:V-PDMS-V: | wt % |  | 11:17:72 | 24:14:62 |
| Sol Fraction (%) | THF |  | — | 8.8 |
|  | IPA |  | 3.6 | 7.6 |
|  | Hexane |  | — | 9.7 |
|  | MeOH |  | — | 2.7 |
|  | H$_2$O |  | 0$^a$ | 0$^b$ (4%$^a$) |
| d$_{sw}$ (%) | THF |  | — | 230 |
|  | IPA |  | 36 | 38 |
|  | Hexane |  | — | 117 |
|  | MeOH$^c$ |  | — | 25.9 |
|  | H$_2$O$^d$ | 1 day | 4.7 | 8.8 |
|  |  | 2 day | 7.1 | 11.4 |
|  |  | 5 days | 8.5 | 14.1 |

$^a$After extraction with IPA (isopropyl alcohol)
$^b$After extraction with hexane and MeOH
$^c$After extraction with hexane
$^d$After extraction with IPA In yet another embodiment a network structure can be formed from a HE$_3$-PEG-HE$_3$ species (see structure 12) according to the following example procedure. Several reagents are added to the reaction mixture set forth in Reaction Scheme 1. Namely, 23 grams (0.005 mol) V-PEG-V (M$_n$=4600 g/mol) dissolved in 100 mL freshly distilled toluene, and 0.44 milligrams Wilkinson's (or Karstedt's) catalyst. The temperature is raised to about 80 to 90° C. for about one day. The progress of the hydrosilation reaction can be followed by $^1$H-NMR (in CDCl$_3$), for example, by the monitoring the disappearance of the V-PEG-V vinyl groups. According to some embodiments m can be an integer from about 2 to about 500. According to other embodiments m can be an integer from about 50 to about 150.

In one embodiment, the present invention relates to a composition, comprising a compound according to the following formula:

wherein each C comprises a crosslinking moiety having at least one epoxide moiety, and each C can be the same or different crosslinking moieties, wherein each B comprises a block and each B can be the same or different blocks, wherein each B is grouped into t groups of B blocks, wherein t is a positive integer from 1 to about 250, and wherein each t group of B blocks is capable of varying, or not varying, in composition relative to other groups of B blocks within a single molecule.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A crosslinking composition comprising a compound according to the following formula:

wherein $X_1$, $X_2$, and $X_3$ are independently selected from linear alkyl chains having from 1 carbon to about 6 carbon atoms, and wherein $Y_1$, $Y_2$, and $Y_3$ are independently selected from linear aliphatic epoxide moieties, linear olefin epoxide moieties, cyclic aliphatic epoxide moieties, cyclic olefin epoxide moieties, or aromatic epoxide moieties.

2. The composition of claim 1, wherein one or more of $Y_1$, $Y_2$, and $Y_3$ are selected from a cyclohexyl epoxide moiety.

3. The composition of claim 1, wherein the composition comprises a compound according to the following formula:

4. The composition of claim 1, wherein the crosslinking composition has a network structure.

* * * * *